United States Patent
Bachand

(10) Patent No.: US 7,312,027 B2
(45) Date of Patent: *Dec. 25, 2007

(54) BINDING ASSAY DEVICE WITH NON-ABSORBENT CARRIER MATERIAL

(75) Inventor: Steven S. Bachand, Dana Point, CA (US)

(73) Assignee: Varian, Inc., Palo Alto, CA (US)

( * ) Notice: Subject to any disclaimer, the term of this patent is extended or adjusted under 35 U.S.C. 154(b) by 328 days.

This patent is subject to a terminal disclaimer.

(21) Appl. No.: 11/071,490

(22) Filed: Mar. 3, 2005

(65) Prior Publication Data

US 2005/0142029 A1    Jun. 30, 2005

Related U.S. Application Data

(62) Division of application No. 10/033,259, filed on Dec. 28, 2001, now Pat. No. 7,049,150.

(51) Int. Cl.
*G01N 33/53* (2006.01)

(52) U.S. Cl. .................... 435/4; 436/514; 436/518; 422/56; 422/58; 422/187; 422/188; 422/104; 422/110; 422/278; 204/400; 204/403.05

(58) Field of Classification Search ............. 436/514, 436/518; 422/56, 58, 187, 188, 104, 110, 422/278; 204/400, 403.05; 435/4
See application file for complete search history.

(56) References Cited

U.S. PATENT DOCUMENTS

| 5,770,458 | A  | * | 6/1998  | Klimov et al. ............. 436/518 |
| 6,180,417 | B1 | * | 1/2001  | Hajizadeh et al. .......... 436/518 |
| 6,194,221 | B1 | * | 2/2001  | Rehg et al. ................. 436/514 |
| 6,194,225 | B1 | * | 2/2001  | Oka et al. ................... 436/518 |
| 6,297,060 | B1 | * | 10/2001 | Nowakowski et al. ...... 436/518 |

OTHER PUBLICATIONS

Millipore's Short Guide for Developing Immunochromatographic Test Strip. pp. 1-37, 1996.*

* cited by examiner

*Primary Examiner*—Bao-Thuy L. Nguyen
(74) *Attorney, Agent, or Firm*—Walter Hackler; Bella Fishman

(57) ABSTRACT

A method of producing a binding assay device provides a porous membrane comprising a material enabling capillary movement of a liquid sample from a first area on the membrane on a second area on the membrane. A detection site is disposed on the membrane between the first and second areas in a non-absorbent medium disposed on the membrane between the detection site and the membrane first area is attached by an adhesion with a dry reagent disposed between the medium and the membrane in order to enable mobilization of the reagent by passage of a liquid sample therepast.

4 Claims, 1 Drawing Sheet

BINDING ASSAY DEVICE WITH NON-ABSORBENT CARRIER MATERIAL

CROSS-REFERENCE TO RELATED APPLICATION

This application is a divisional of application Ser. No. 10/033,259 filed on Dec. 28, 2001 now U.S. Pat. No. 7,049,150.

BACKGROUND OF THE INVENTION

The present invention is generally related to test devices for performing binding assays for determining characteristics of a sample, such as a biological liquid. More particularly, the present invention is directed to assays, which utilize porous carrier materials for transporting reagents.

The device is in the form of test strips commonly utilized in the analysis of various types of samples, particularly, biological fluids, because of their convenience and rapid determination of results. Test strips assays for detecting various clinically significant substances and biological fluids, such as urine and serum, have been very advantageous in assisting the diagnosis and treatment of disease states.

Many binding assay formats are well known in the art and include competition, sandwiched and agglutination assays.

A thorough discussion of prior art assay devices is set forth in U.S. Pat. No. 5,770,458. These assays commonly use test strips comprising an absorbent, porous matrix incorporated with indicator reagents usually of a colorimatrix type. The sample to be tested is contacted with reagent matrix and the indicator response is observed after a certain period of time. Combinations of test strips enable simultaneous test reactions to proceed.

A problem associated with prior art devices, as pointed out in the cited references, is their lack of uniform mobilization of reagents for migration through the strip. The cited reference utilizes a complicated multi-membrane configuration for introducing reagents, which depends upon parallel liquid migration of liquid sample through co-joined membranes.

The present invention provides for a device and procedure for introducing a binding reagent into a strip absorbent membrane in a binding assay device.

SUMMARY OF THE INVENTION

A binding assay in accordance with the present invention generally includes a porous medium comprising a material enabling capillary movement of a liquid sample from a first area of the membrane to a second area of the membrane. A detection site is disposed in the membrane between the first and second areas and a non-absorbent medium is disposed on the membrane between the detection site and the membrane first area with the medium being attached to the membrane by an adhesive.

A dry reagent is disposed between the medium and the membrane in order to enable mobilization of the reagent, by passage of the liquid sample, and entry into the membrane and the liquid sample before the liquid sample reaches the detection site.

Preferably, the dry agent disposed between the adhesive and the membrane are disposed in the form of a stripe, with the stripe, being generally transverse to a direction of the sample migration. Preferably, the stripe is aligned perpendicular to the sample migration direction.

More particularly, the medium, which may be polyester film MYLAR® is in the form of a strip having a width greater than a width of reagent stripe. MYLAR® is a bi-axially oriented, thermoplasitc film made from ethylene glycol and dimethyl terephthalate (DMT) and manufactured by DuPont Teijin Film (Hopewell, Va., USA). It should be appreciated that the medium, while referenced to as MYLAR® may be any polyester, PET or any other label stock well known for adhesive substitution and that reference to polyester film MYLAR® includes all such alternative mediums. In addition, the membrane is also preferably in the form of a strip having a width at least as wide as the medium width.

The reagent preferably is particle based in an aqueous buffer solution and the dry reagent is adhered only by the adhesive coated polyester film MYLAR®. In addition, the dry reagent preferably comprises between about 2% and about 30% w/v sugar with the sugar preferably being a crystalline sugar, such as for example, sucrose or mixtures thereof. A method in accordance with the present invention of producing a binding assay device generally includes the steps of providing a porous membrane material enabling capillary movement of a liquid sample from a first area of membrane to a second area of the membrane.

The method further includes disposing a detection site on the membrane between the first and second areas and providing a non-absorbent medium having a bottom side with an adhesive disposed on the bottom side.

A particle based (i.e. antibody conjugated to colloidal gold) liquid reagent is disposed on the medium and evaporated to provide a dry reagent on the medium bottom side. The device is completed by adhering the medium bottom side to the membrane between the first area and the detection site.

More particularly, the non-porous medium is provided with an adhesive covering the entire medium bottom side and the solublized reagent is disposed onto the adhesive. Preferably, the evaporated reagent is in the form of a bead along the non-porous medium and the step of evaporating the solublized reagent results in a stripe of dry semi-crystallized reagent along the medium.

In one embodiment of the present invention, the step of evaporating solvent includes evaporating the water solvent and the suspended particle reagents includes a concentration of sugar.

Through the use of sugar concentration in amounts between about 2% and about 30% w/v in the particle based reagent, control of the mobilization rate of the reagent into the membrane upon passage or the liquid sample therepast is enabled.

The medium may be a polyester MYLAR® tape and the concentration of sugar in the solublized reagent may also be provided to control the viscosity of the solublized reagent applied in bead form to prevent collapse or separation of the bead upon movement of the medium and drying of the solublized reagent.

BRIEF DESCRIPTION OF THE DRAWINGS

The advantages and features of the present invention will be better understood by the following description when considered in conjunction with the accompanying drawings in which.

DETAILED DESCRIPTION

Figure 1:
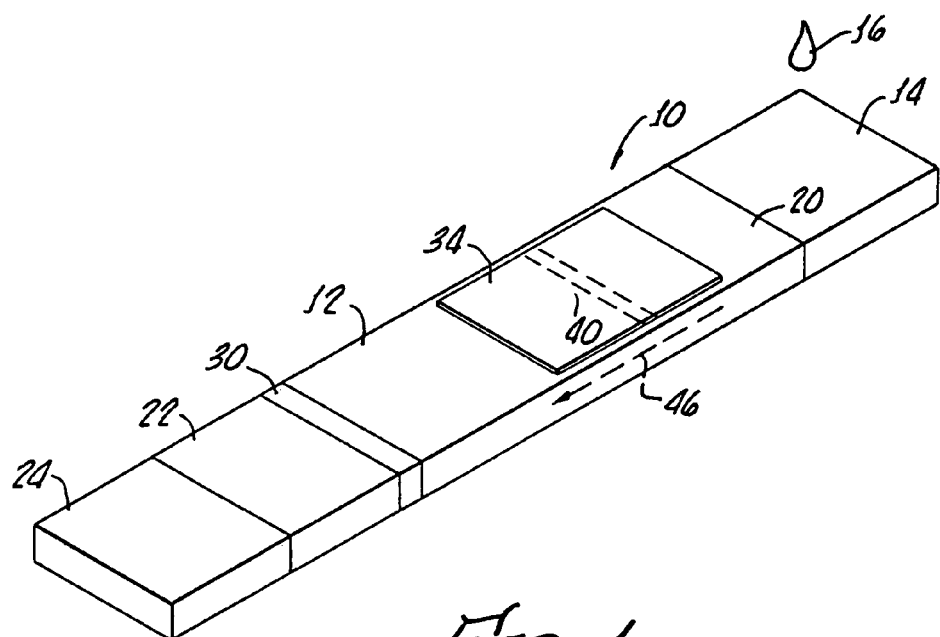
FIG. 1 is a perspective of a binding assay device in accordance with the present invention generally showing a porous membrane, a detection site thereon, a sample pad, and end pad along with a non-porous medium attached to the membrane between the sample pad and the detection site, which includes a dry reagent in contact with the membrane for enabling mobilization thereof as liquid sample passes thereby.
Figure 2:
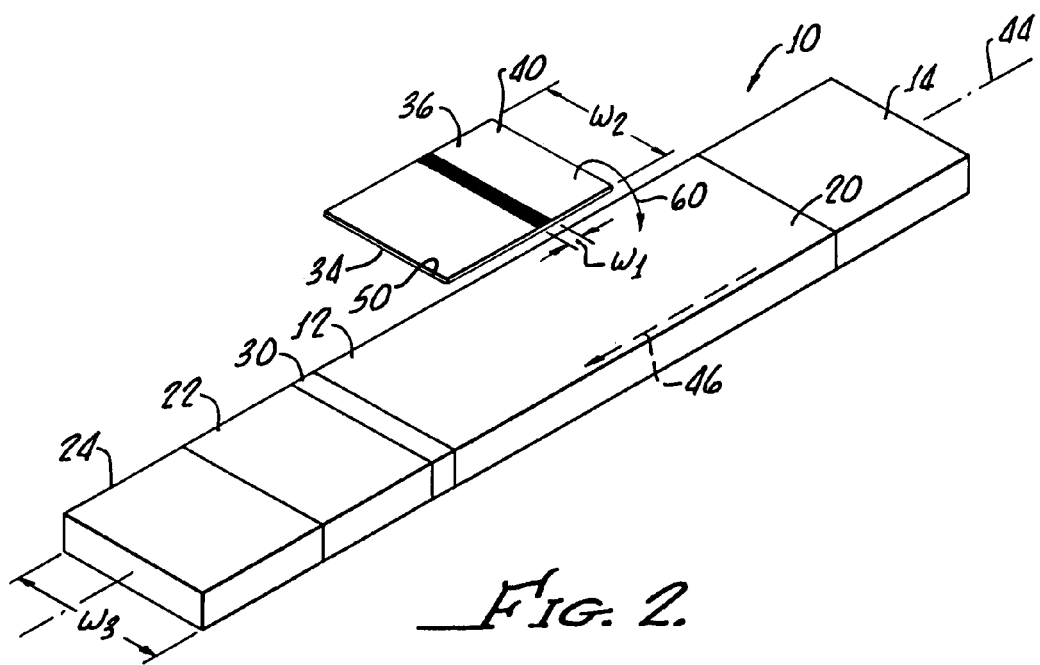
FIG. 2 is a perspective view similar to FIG. 1 illustrating a method of the present invention.

With reference to FIGS. 1 and 2, a binding assay device 10 in accordance with the present invention, generally includes a porous medium 12 which may be in the form of a strip as shown. The membrane may be supported in a holder, not shown, in any conventional manner. The membrane may be formed from any bibulous or fibrous material capable of capillary action. Specific examples include thin layer chromatography materials, paper or cellulose, porous synthetic plastics including nitro-cellulose and nylon. A sample pad 14 may be provided for receiving a liquid sample 16 and wicking the sample into the membrane 12. As hereinabove noted, the membrane comprises a material enabling capillary movement of the liquid sample 16 from a first area 20 adjacent the sample pad to a second area 22 adjacent and absorbent end pad 24 which may be formed from any suitable absorbent material.

A detection site is formed, or disposed in the membrane 12 in any conventional manner. The detection site may include, for example but not limited to, an antibody as found in sandwich assays or a drug—BSA conjugate (drug—protein carrier) as found in competitive inhibition assays.

A non-absorbent medium, such as, for example, MYLAR® 34 is disposed on the membrane 12 between the first area 20 and the detection site 30 with the medium 34 being adhered to the membrane 12 by an adhesive 36. The adhesive 36, may be any conventional pressure sensitive acrylic based adhesive and preferably, covers an entire surface of the medium 34, although, such coverage is not required.

A dry reagent 40 is disposed between the medium 34 and the membrane 12, and preferably, disposed onto the adhesive 36, underside the medium 34, in the form of a bead, or stripe having a width $W_1$ smaller than a width $W_2$ of the medium 36. The reagent strip 40 is preferably aligned generally normal to a longitudinal axis 44 of the membrane 12 in a direction of the sample migration (indicated by the dashed arrow 46).

The membrane 12 is also preferably in the form of a strip which includes a width $W_3$ which may be equal or greater than the medium width $W_2$ both of which are significantly greater than the reagent stripe width $W_1$. The relative widths of the medium 36 membrane 12 and stripe 40 may be adjusted for controlling mobilization of the reagent in the strip 40 into the membrane as the liquid sample 16 migrates by wicking action therepast as indicated by the arrow 46.

As will be hereinafter discussed in connection with the method in accordance with the present invention, the reagent stripe 40 may comprise sugars in a crystalline form in order to enable the stripe to be laid down on the medium 34 and adhesive 36 in form of a liquid bead that will not collapse upon minor movement of the membrane 12 and medium and during drying thereof. The concentration of sugar is adjusted to control the rate of mobilization from the stripe 40 into the medium which enables adjustment of the sensitivity of the test being performed by the device.

The method of the present invention includes the providing of the porous membrane 12 along with disposing the detection site thereon as well as providing a non-absorbent medium, such as polyester film MYLAR® having a bottom side 50 with the adhesive 36 disposed thereon.

The reagent stripe 40 is formed by disposing a particle based reagent on the adhesive 36 and evaporating a solvent therefrom, preferably water, to provide the dry reagent strip 40.

A formulation of the particle based reagent may comprise an antibody conjugated to a colloidal gold particle in the size range, for example, of 30-60 nanometers in a buffered sucrose solution in the 2-30 percent w/v range. A non-crystalline sugar, like fructose, can be added in a lower percentage to prevent or minimize cracking of the reagent bead upon drying down on the adhesive substrate.

A sugar concentration in the range of 2% to 30% w/v is provided in order to enable a liquid bead that will not collapse or separate upon movement of the medium 36 and membrane 12 and during drying thereof. For example, a sugar concentration of about 10% enables a bead having a width of about 0.05 inches to be formed due to the viscosity provided by the sugar concentration. This is also dependent on the rate and volume of reagent application.

In addition, it is preferable that a sugar such as fructose be utilized that does not crystallize. Fructose can be mixed with a larger proportion of other sugars such as sucrose may be used to prevent excessive cracking as the reagent bead dries on the substrate.

Following the disposition of the reagent 40 onto the medium 34 and adhesive 36 and drying thereof, the medium 34 may be inverted, as indicated by the arrow 60 and adhered to the medium 12 by the adhesive 36. The structure of the present invention will tend to eliminate to the undesired reagent retention seen with conventional conjugate release materials, thus increasing the repeatability of lateral flow assays.

Although there has been hereinabove described a binding assay device and method in accordance with the present invention for the purpose of illustrating the manner in which the invention may be used to advantage, it will be appreciated that the invention is not limited thereto. Accordingly, any and all modification, variations or equivalent arrangements which may occur to those skilled in the art should be considered to be within the scope as defined in the appended claims.

What is claimed is:

1. A method of producing a binding assay device, said method comprising the steps of:
   providing a porous membrane comprising a material enabling capillary movement of a liquid from a first area of the membrane to a second area of the membrane;
   disposing a detection site on the membrane between the first and second areas;
   providing a non-absorbent medium having a bottom side with an adhesive disposed on the bottom side;
   disposing a soulblized reagent onto the adhesive;
   evaporating a solvent in a particle based reagent to provide a dry reagent on the adhesive; and
   adhering the medium bottom side to a top side of the membrane between the first area and said detection site.

2. The method according to claim 1, wherein the non-porous medium is provided with adhesive covering an entire medium bottom side.

3. The method according to claim 2, wherein the evaporated reagent is disposed as a bead along the non-porous medium and the step of evaporation the solvent results in a stripe of dry reagent along the medium.

4. The method according to claim 3, wherein the step of evaporating the solvent includes evaporating a water solvent.

* * * * *